(12) United States Patent
Matsumoto et al.

(10) Patent No.: US 8,654,323 B2
(45) Date of Patent: Feb. 18, 2014

(54) ANALYZING APPARATUS

(75) Inventors: Daisuke Matsumoto, Kyoto (JP);
Yasunori Shiraki, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 217 days.

(21) Appl. No.: 13/241,960

(22) Filed: Sep. 23, 2011

(65) Prior Publication Data
US 2012/0075623 A1 Mar. 29, 2012

(30) Foreign Application Priority Data
Sep. 27, 2010 (JP) ................... 2010-215071

(51) Int. Cl.
*G01J 1/00* (2006.01)
(52) U.S. Cl.
USPC ............ 356/213; 356/432; 356/246; 356/244
(58) Field of Classification Search
USPC .................................. 356/213, 432, 246, 244
See application file for complete search history.

(56) References Cited

U.S. PATENT DOCUMENTS

| | | | |
|---|---|---|---|
| 5,302,272 A | 4/1994 | Klein | |
| 6,069,694 A | 5/2000 | VonBargen | |
| 7,301,633 B2 * | 11/2007 | Gibbs et al. | 356/369 |
| 2008/0124247 A1 * | 5/2008 | Matsuoka et al. | 422/82.08 |
| 2009/0109433 A1 * | 4/2009 | Matsumoto | 356/244 |

FOREIGN PATENT DOCUMENTS

| | | |
|---|---|---|
| EP | 0679885 A2 | 11/1995 |
| EP | 1640704 A2 | 3/2006 |
| EP | 1985992 A1 | 10/2008 |
| EP | 2352035 A1 | 8/2011 |
| JP | 2004-117302 A | 4/2004 |
| JP | 2006-300721 A | 11/2006 |
| WO | 2010/010904 A1 | 1/2010 |

* cited by examiner

*Primary Examiner* — Tarifur Chowdhury
*Assistant Examiner* — Isiaka Akanbi
(74) *Attorney, Agent, or Firm* — Fox Rothschild LLP

(57) ABSTRACT

An analyzing apparatus includes a microchip, a detecting unit and an analyzing-measuring unit. The microchip is formed of a light transmissive material formed with a separation fluid channel that is a light measuring part. The detecting unit includes an emitted-light guiding unit that emits light to the separation fluid channel, and a received-light guiding unit that receives light through the separation fluid channel. The emitted-light guiding unit or the received-light guiding unit placed at a position facing a microchip support table via the microchip abuts the microchip, and pushes the microchip in a direction toward the microchip support table. The analyzing-measuring unit includes the detecting unit, the emitted-light guiding unit and the received-light guiding unit, and detects a constituent of a sample filled in the separation fluid channel.

19 Claims, 5 Drawing Sheets

ANALYZING APPARATUS

CROSS-REFERENCE TO RELATED APPLICATION

This application claims the benefit of Japanese Patent Application No. 2010-215071 filed on Sep. 27, 2010, the entire disclosure of which is incorporated by reference herein.

FIELD

The present invention relates generally to an analyzing apparatus, and more particularly, to an analyzing apparatus that detects constituents of a sample filled in a fluid channel through an optical scheme.

BACKGROUND

Recently, analyses, such as gene analysis, clinic diagnosis, and drug screening, using a microchip device (a micro-fluid device) are established in the fields of chemistry, biochemistry, pharmaceutical science, medical science, and veterinary science.

An example analysis method of analyzing the concentration or the amount of a specific constituent contained in a sample is a method including a separating process of separating the specific constituent from the sample and a process of detecting the separated specific constituent. For example, in the case of an analysis method through a capillary electrophoresis technique, a migration solution is filled in a separation fluid channel of a microchip device, and a sample is introduced in one-end side of the separation fluid channel. Upon application of a voltage across both ends of the separation fluid channel, an electroosmotic flow of causing the migration solution to move from the positive side to the negative side is generated. Moreover, by the application of the voltage, the specific constituents attempt to move in accordance with respective electrophoretic levels. Hence, the specific constituent moves in accordance with a velocity vector generated by a synthesis of the velocity vector of the electroosmotic flow and the velocity vector of the movement by electrophoresis. This movement separates the specific constituent from other constituents. When the separated specific constituent is detected by, for example, an optical scheme, the amount or the concentration of the specific constituent can be analyzed.

Unexamined Japanese Patent Application KOKAI Publication No. 2004-117302 discloses a compact micro-chemical system which needs no alignment of optical axes and which has a high measurement sensitivity. The micro-chemical system includes a tabular member with a fluid channel filled with a liquid sample, an optical fiber with a lens, a light source unit that emits excitation light and detection light, and a detecting apparatus. The optical fiber with the lens includes a gradient index rod lens, and an optical fiber having one end connected to the gradient index rod lens and another end connected to the light source, and an FC connecter provided in the halfway therebetween. The FC connector includes FC plugs and adaptors fixing respective FC plugs, and is coupled together by screwing the FC plugs into respective adaptors.

Unexamined Japanese Patent Application KOKAI Publication No. 2006-300721 discloses a thermal lens spectroscopic analyzing system and a thermal lens signal correcting method which can precisely measure a sample even if a thermal lens signal intensity is changed due to an external environmental change. According to such technologies, the thermal lens spectroscopic analyzing system includes a micro-chemical chip formed with grooves in which a liquid sample is filled, a gradient index rod lens which collects excitation light and detection light propagated from a light source unit in the liquid sample through an optical fiber and which generates a thermal lens signal, and a photoelectric converter that detects respective light intensities of the excitation light and the detection light and the intensity of the thermal lens signal. The measured value of the intensity of the thermal lens signal is corrected by integrating the measured value of the intensity of the thermal lens signal (the predetermined intensity of the excitation light/the measured intensity of the excitation light) and/or a second ratio (the predetermined intensity of the detection light/the measured intensity of the detection light).

International Application Publication No. WO 2010/010904 A discloses an analyzing apparatus that includes an optical fiber which guides light from a light source to a microchip. The analyzing apparatus employs a configuration in which a ferrule holding an end of the optical fiber for guiding the light from the light source to the microchip is held so as to be movable in the vertical direction while being maintained in a condition biased by a coil spring in a holder, and abuts the microchip.

SUMMARY

As an analysis method through an optical scheme like the above-explained prior arts, various devisal are made in order to improve the detection precision, such as a position of emitting light and collection of the light. However, a thermal effect when a light emitting side is controlled is concerned but a thermal effect when a light receiving side is controlled is out of the consideration.

In the case of a separation through an electrophoresis technique, in addition to the thermal effect by light emission, a heat is generated by applying a voltage to the microchip (across both ends of the separation fluid channel), so that the microchip may be deformed by such heat and the analysis precision may decrease. In particular, in the case of the microchip device formed of a resin, the problem of deformation is noticeable.

Moreover, when the sample to be analyzed is a blood or a protein, denaturation due to heat may occur. Furthermore, because of the thermal effect, air bubbles may be produced in the separation fluid channel of the microchip device, so that the analysis precision may decrease.

The microchip device is controlled in a cooled condition in some cases in order to suppress such thermal effect, in this case, however, the temperature gradient between the interior of the microchip device and the external surface thereof becomes large due to such a cooling control, and as a result, the deformation of the microchip device may be promoted.

Moreover, heat is generated during a reaction of a sample, and it is necessary in some cases to cool such heat. When the microchip device is deformed due to the heat itself generated during the reaction of the sample, and thus the microchip device is controlled in a cooled condition, because of a temperature gradient between the internal heat generating portion and the cooling portion, the deformation of the microchip device is promoted.

In a measurement through a sample reaction, an analysis is performed in some cases through an optical scheme while the temperature of the microchip device is adjusted. When, for example, an enzyme sample is used, it is desirable to adjust the temperature of the microchip device to be around 37 degrees Celsius which has a high reactivity. In this case, during a temperature rise from the initial temperature of the microchip (e.g., a room temperature like around 20 degrees Celsius) to 37 degrees Celsius, the microchip device may be deformed.

As explained above, regardless of cooling and heating, when a change in a temperature occurs from the interior or the exterior of the microchip device, the microchip device may be deformed due to such a temperature change.

The present invention has been made in view of the above-explained circumstance, and it is an object of the present invention to provide an analyzing apparatus which reduces a thermal effect and which suppresses deterioration of the measurement precision.

An analyzing apparatus according to an aspect of the present invention includes: a microchip including a light measuring part; a support member that supports the microchip; a light emitting unit that emits light to the light measuring part; a light receiving unit that receives light which has gone through the light measuring part; and a first force-applying member which causes the light emitting unit or the light receiving unit that is placed at a position facing the support member via the microchip to abut the microchip and to push the microchip in a direction in which the microchip is supported by the support member.

BRIEF DESCRIPTION OF THE DRAWINGS

A more complete understanding of this application can be obtained when the following detailed description is considered in conjunction with the following drawings, in which.

DETAILED DESCRIPTION

<Embodiments>

Figure 1:
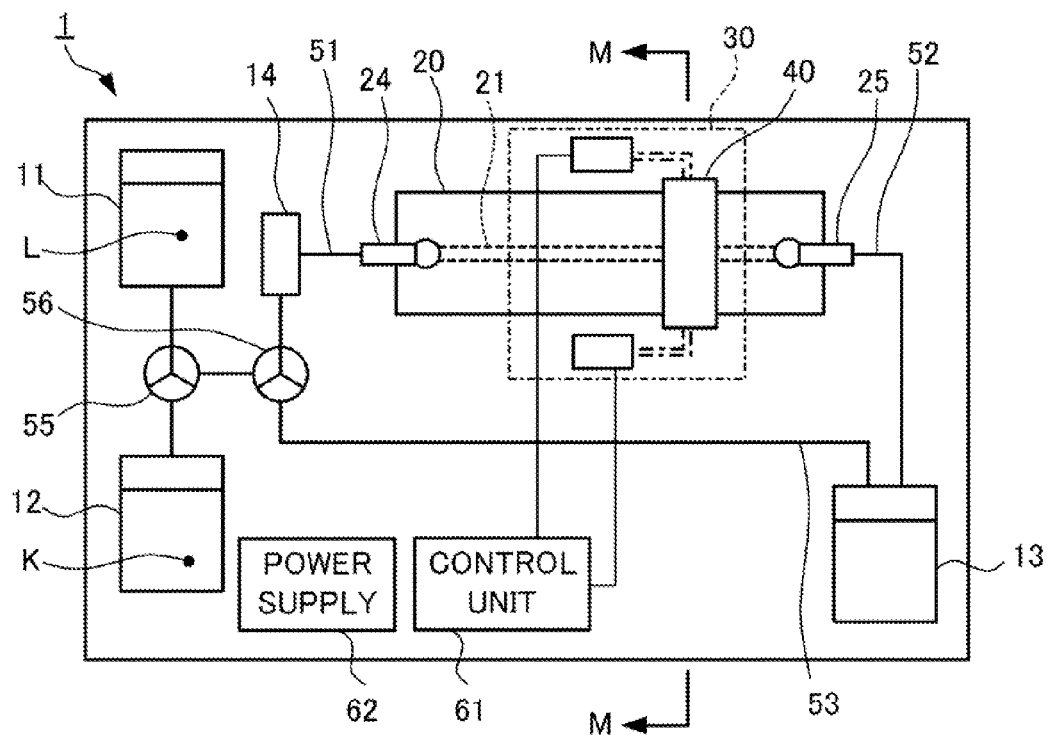
FIG. 1 is a schematic configuration diagram showing an illustrative analyzing apparatus according to an embodiment of the present invention.

FIG. 1 is a schematic configuration diagram showing an illustrative analyzing apparatus according to an embodiment of the present invention. In the present embodiment, an analyzing apparatus 1 performs an analysis through a capillary electrophoresis technique, and performs detection through an optical scheme.

The analyzing apparatus 1 includes a liquid reserve tank 11, a sample tank 12, a waste liquid tank 13, a dispensing unit 14, a microchip 20, electrodes 24 and 25, an analyzing-measuring unit 40 with a detecting unit 30, a fluid channel 51 or a fluid channel 53, three-way valves 55 and 56, a control unit 61 and a power supply 62. The microchip 20 is formed with a separation fluid channel 21 an inlet opening 22 and an outlet opening 23 (see FIG. 2A).

The liquid reserve tank 11 reserves a reserved liquid L, e.g., a migration solution, purified water, or a rinse solution. The migration solution functions as a buffer, and example of such a migration solution is a water solution of 100 mM malic-acid-arginine buffer (pH 5.0)+1.5% chondroitin-sulfuric-C-sodium.

The sample tank 12 reserves a sample solution K. The sample solution K contains specific constituents to be analyzed by the analyzing apparatus 1. The sample solution K is a liquid having undergone a treatment appropriate for a measurement, e.g., dilution or mixing.

The waste liquid tank 13 reserves a liquid already used. The dispensing unit 14 fills the sample solution K in the sample tank 12 into the separation fluid channel 21 of the microchip 20.

Figure 2A:
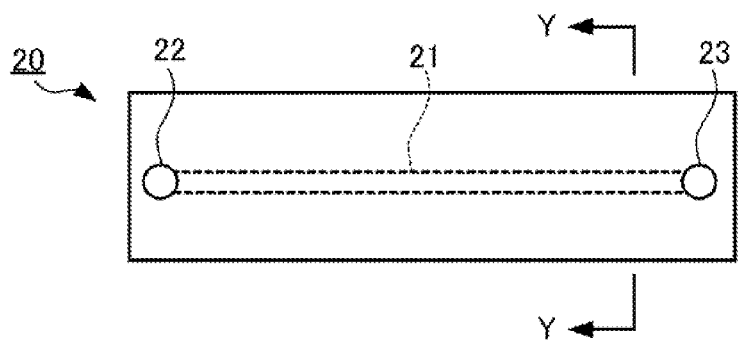
FIG. 2A is a plan view showing an illustrative microchip according to the embodiment.
Figure 2B:
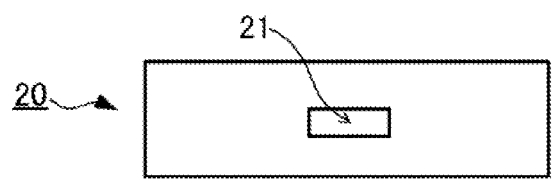
FIG. 2B is a cross-sectional view taken along a line Y-Y in FIG. 2A.

FIG. 2A is a plan view showing an illustrative microchip shown in FIG. 1. FIG. 2B is a cross-sectional view taken along a line Y-Y of FIG. 2A.

The microchip 20 includes the separation fluid channel 2.1 that is a minute fluid channel, and the inlet and outlet openings 22 and 23 for introducing and discharging a solution from and to the separation fluid channel 21. The microchip 20 is formed by joining two resin-made substrates that are light transmissive materials. The microchip 20 is formed of a resin, such as a silicon resin, an acrylic resin like a methyl-methacrylate resin, a polystyrene resin, or a polycarbonate resin.

The separation fluid channel 21 of the microchip 20 is a field where an analysis through a capillary electrophoresis technique is performed. It is preferable that the cross section of the separation fluid channel 21 should be a circle with a diameter of 25 to 100 μm, or a rectangular with a side of 25 to 100 μm. The present invention is not limited to such numerical data as long as it has a shape and a dimension appropriate for capillary electrophoresis. In the present embodiment, the separation fluid channel 21 has a length of 30 mm or so, but the present invention is not limited to such numerical data.

The separation fluid channel 21 is communicated with the inlet opening 22 and the outlet opening 23. The inlet opening 22 is provided at one end of the separation fluid channel 21, and the sample solution K is introduced therein from the dispensing unit 14. In the present embodiment, in addition to the sample solution K, the reserved liquid L, such as a migration solution, purified water, or a rinse solution, can be introduced from the inlet opening 22. The outlet opening 23 is provided at another end of the separation fluid channel 21, and the sample solution K or the reserved liquid L filled in the separation fluid channel 21 is discharged from the outlet opening 23.

Moreover, the separation fluid channel 21 has the electrodes 24 and 25 provided at respective ends. In the present embodiment, the electrode 24 is exposed in the inlet opening 22, rand the electrode 25 is exposed in the outlet opening 23.

Figure 3:
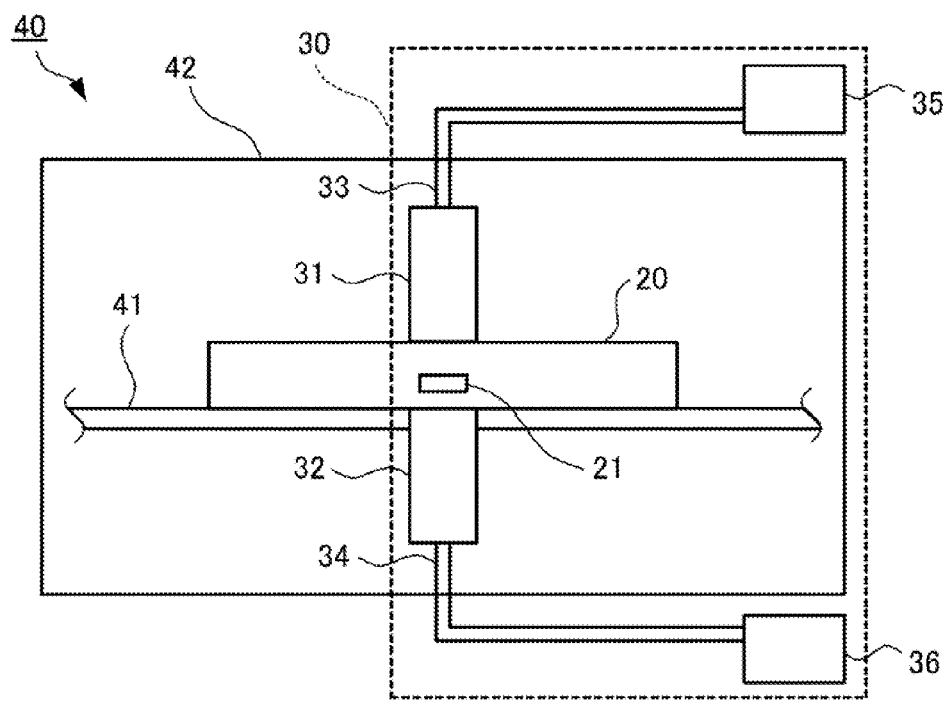
FIG. 3 is a partial enlarged view showing an illustrative analyzing-measuring unit of the analyzing apparatus according to the embodiment.

FIG. 3 is a partial enlarged view showing an illustrative analyzing-measuring unit of the analyzing apparatus according to the present embodiment. FIG. 3 shows an outline of a cross section taken along a line M-M in FIG. 1.

An analyzing-measuring unit 40 includes the microchip 20, the detecting unit 30, a microchip support table 41, and a shield wall 42. It is preferable that a light-emission control unit 35 and a light-reception control unit 36 which configure the detecting unit 30 should be provided so as to be apart from the microchip 20 at a predetermined distance and laid out in a different space surrounded by a material blocking light. The light-emission control unit 35 and the light-reception control unit 36 may be provided separately as shown in FIG. 3 or may be integrated together as a solo emitted-light/light-reception control unit.

More specifically, for example, a designing is made so that the microchip 20 is disposed in the interior of the shield wall 42, and the light-emission control unit 35 and the light-reception control unit 36 are disposed outside the shield wall 42. The light-emission control unit 35 is connected to an emitted-light guiding unit 31 through an optical fiber 33, and the light-reception control unit 36 is connected to a received-light guiding unit 32 through an optical fiber 34. The optical fibers 33 and 34 are silica-glass optical fibers for example.

Figure 4A:
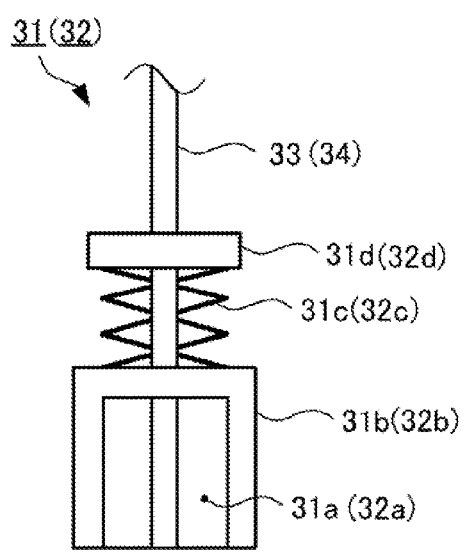
FIG. 4A is a schematic configuration diagram showing an illustrative light guiding unit of a detecting unit according to the embodiment.

FIG. 4A is a schematic configuration diagram showing an illustrative light guiding unit of the detecting unit according to the present embodiment. The emitted-light guiding unit 31 includes a ferrule 31a, a holder 31b, a coil spring 31c and a stopper 31d. The ferrule 31a is fixed to an end of the optical fiber 33 so as not to disturb guiding of light. The ferrule 31a is formed of a ceramic like zirconia. The ferrule 31a of the emitted-light guiding unit 31 and the optical fiber 33 are collectively referred to as a light emitting unit.

The stopper 31d of the emitted-light guiding unit 31 is not fixed to the optical fiber 33 but slides in accordance with an expansion/contraction of the coil spring 31c. By fixing the stopper 31d, the ferrule 31a of the emitted-light guiding unit 31 can slide against the stopper 31d.

The stopper 31d of the emitted-light guiding unit 31 is fixed to a part of the shield wall 42 where a force (a force FE see FIG. 5) of pushing the emitted-light guiding unit 31 against the microchip 20 via the tip of the emitted-light guiding unit 31 (the ferrule 31a) can be applied when, for example, the emitted-light guiding unit 31 contacts the microchip 20. When the microchip 20 is disposed in the analyzing apparatus 1, the coil spring 31c receives a force in a contraction direction, and the restorative force (the force F1) can be applied to the microchip 20.

Figure 4B:
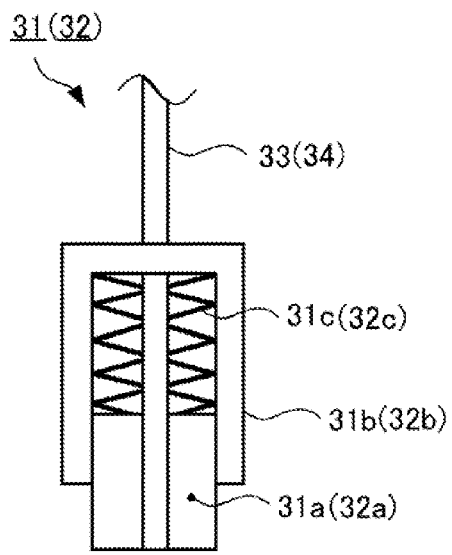
FIG. 4B is a schematic configuration diagram showing another illustrative light guiding unit according to the embodiment.

FIG. 4B is a schematic configuration diagram showing another illustrative light guiding unit according to the present embodiment. The light guiding unit 31 shown in FIG. 4B employs a configuration in which the holder 31b of the emitted-light guiding unit 31 shown in FIG. 4A also serves as the stopper 31d.

The holder 31b of the emitted-light guiding unit 31 is not fixed to the ferrule 31a and the optical fiber 33, but slides against the optical fiber 33 in accordance with an expansion/contraction of the coil spring 31c. By fixing the holder 31b, the ferrule 31a of the emitted-light guiding unit 31 is allowed to slide.

The holder 31b of the emitted-light guiding unit 31 is fixed to a part of the shield wall 42 where a force (the force F1) of pushing the emitted-light guiding unit 31 against the microchip 20 via the tip of the emitted-light guiding unit 31 (the ferrule 31a) can be applied when, for example, the emitted-light guiding unit 31 contacts the microchip 20. When the microchip 20 is disposed in the analyzing apparatus 1, the coil spring 31c receives a force in a contraction direction, and the restorative force (the force F1) can be applied to the microchip 20.

The emitted-light guiding unit 31 may include a lens at the tip of the ferrule 31a. In addition to the lens, the emitted-light guiding unit 31 may include any one of a filter and a housing.

FIGS. 4A and 4B also show the configuration of the received-light guiding unit 32. A ferrule 32a of the received-light guiding unit 32 and the optical fiber 34 configure a light receiving unit.

The received-light guiding unit 32 needs no force-applying member when no pressure is applied to the microchip 20, and may be configured by only the ferrule 32a.

The received-light guiding unit 32 needs a force-applying member when a pressure is applied to the microchip 20. An elastic mechanism that is the force-applying member is basically the same configuration as that of the emitted-light guiding unit 31, and a spring mechanism including a coil spring 32c is employed. The received-light guiding unit 32 may include a lens at the tip of the ferrule 32a. Moreover, in addition to the lens, the received-light guiding unit 32 may include any one of a filter and a housing.

In FIGS. 3, 4A and 4B, the explanation is given of an example case in which the emitted-light guiding unit 31 is located at a position facing the microchip support table 41 via the microchip 20. In this case, it is preferable in the present embodiment that the emitted-light guiding unit 31 should include a force-applying member and the received-light guiding unit 32 should include a force-applying member with a weaker force than that of the force-applying member of the emitted-light guiding unit 31.

When the emitted-light guiding unit 31 and the received-light guiding unit 32 are located at inversed locations, i.e., when the received-light guiding unit 32 is located at a position facing the microchip support table 41 via the microchip 20, the received-light guiding unit 32 facing the microchip support table 41 is equipped with a force-applying member. More preferably, the emitted-light guiding unit 31 has a force-applying member with a weaker force than that of the force-applying member of the received-light guiding unit 32. In both cases, it is appropriate if a force of pressing the microchip 20 against the microchip support table 41 can be applied through a light guiding unit located at a position facing the microchip support table 41.

When the analyzing apparatus 1 performs analysis, a voltage is applied across both electrodes 24 and 25 located at both ends of the separation fluid channel 21, respectively, in order to perform electrophoresis, the temperature of the microchip 20 itself rises. When the temperature of the microchip 20 rises, due to a temperature rise in the separation fluid channel 21, the temperature of the buffer solution exceeds a predetermined temperature so that moistened spots may be produced or denaturation like protein coagulation occurs when the measurement target is a blood, which affects the measurement, and thus the measurement precision decreases. Moreover, minute deformation is produced in the microchip 20 itself, relative positions of the light emitting and receiving devices, i.e., the distance between the emitted-light guiding unit 31 and the received-light guiding unit 32 varies, so that the measurement precision decreases.

Hence, it is desirable that the temperature rise of the microchip 20 should be made gradual as much as possible, so as not to exceed the predetermined temperature as much as possible, and the microchip support table 41 should be formed of a material with a high thermal conductivity like aluminum so as to facilitate heat dissipation. Furthermore, a Peltier device, etc., is provided in order to perform cooling control, or such cooling control may be carried out by air cooling by a fan motor.

In the case of a measurement method with a technique other than electrophoresis, e.g., an enzyme reaction sample, a temperature control may be carried out around the temperature of 37 degrees Celsius in order to eliminate the environmental temperature effect to the sample reaction. Moreover, a cooling control may be carried out in order to suppress a heat generation during the sample reaction.

That is, when a measurement through the microchip 20 is performed, a measurement cell or a capillary itself is subjected to a temperature change, and the temperature change affects the measurement precision, and a temperature is controlled to a desired temperature in order to suppress the effect of the temperature change. In those cases, the interior and the exterior of the microchip 20 deform due to the effect of the temperature change.

When an analysis and a measurement are performed using the analyzing apparatus 1, the light-emission control unit 35 and the light-reception control unit 36 are activated and a detection is performed by the detecting unit 30. At this time, the light-emission control unit 35 and the light-reception control unit 36 generate heats, so that there is a thermal effect to the microchip 20.

Conversely, the light-emission control unit 35 and the light-reception control unit 36 are easily affected by heat. When the characteristic of a light receiving device or that of a light emitting device and the characteristic of a control circuit driving those change due to thermal effects from the microchip itself and an element for controlling the temperature of the microchip, the amount of received light and the amount of emitted light change, resulting in an error contained in a measured value. In general, the amount of emitted light can be corrected based on a monitoring of reference light, but the amount of received measurement light itself cannot be directly corrected, affecting the measurement precision.

Moreover, there are effects of electrical noises generated from an element for a temperature control and the microchip itself. Furthermore, noises may mutually affect between the light-emission control unit 35 and the light-reception control unit 36.

Hence, it is preferable that the light-emission control unit 35 and the light-reception control unit 36 should be distant from the microchip 20 in order to reduce the thermal effect from the light-emission control unit 35 and the light-reception control unit 36 to the microchip 20 and the thermal effect from the microchip 20 to the light-emission control unit 35 and the light-reception control unit 36.

As an environment which is not likely to be affected by an external temperature, for example, a space surrounded by the shield wall 42 is provided and the microchip 20 is placed in the space inside the shield wall 42. Heats from the light-emission control unit 35 and the light-reception control unit 36 both located outside the shield wall 42 are not likely to be transferred to the microchip 20 placed inside the shield wall 42, and thus a thermal effect to the microchip 20 can be suppressed. Moreover, the shield wall 42 can suppress stray light at the time of emitting/receiving light. The shield wall 42 not only suppresses the temperature rise of the microchip 20 in order to reduce a thermal effect to a measurement but also improves the measurement precision by eliminating stray light.

Furthermore, the light-emission control unit 35 and the light-reception control unit 36 are connected to the emitted-light guiding unit 31 and the received-light guiding unit 32, respectively, through the optical fibers 33 and 34, etc . . . By using the light guiding units like the optical fibers 33 and 34, the light-emission control unit 35 and the light-reception control unit 36 can be placed so as to be distant from the emitted-light guiding unit 31 and the received-light guiding unit 32, respectively, and thus the thermal effect can be reduced. Moreover, by using the optical fibers 33 and 34, the good workability when the microchip 20 is disposed at an analyzing-measuring location can be obtained.

The optical fiber 34 can be used not only at the light emitting side but also at the light receiving side. For example, when the light-reception control unit 36 uses a photo diode as the light receiving device, it is preferable that the received-light guiding unit 32 should have a thermal change as little as possible since the photosensitivity of the photo diode has a temperature characteristic. When no optical fiber 34 is used at the light receiving side, the received-light guiding unit 32 is affected by heat generated by the light-reception control unit 36, a temperature change occurs, and thus the measurement precision of received light decreases. By using the optical fiber 34, the thermal effect from the light-reception control unit 36 to the received-light guiding unit 32 can be reduced, thereby suppressing a deterioration of the measurement precision.

It is preferable that the analyzing-measuring unit 40 should have the electrodes 24 and 25 formed at both ends of the separation fluid channel 21, respectively, and outside the shield wall 42. In addition to the layout of the light-emission control unit 35 and the light-reception control unit 36 outside the shield wall 42, if the electrodes 24 and 25 are also laid out outside the shield wall 42, the temperature rise inside the shield wall 42 can be suppressed, and thus the temperature rise of the microchip 20 can be suppressed, thereby suppressing a deterioration of the measurement precision as a result.

The detecting unit 30 includes the emitted-light guiding unit 31, the received-light guiding unit 32, the optical fibers 33 and 34, the light-emission control unit 35 and the light-reception control unit 36. The detecting unit 30 analyzes specific constituents separated from the sample solution K in the separation fluid channel 21. The emitted-light guiding unit 31 and the received-light guiding unit 32 in the detecting unit 30 are provided at portions near the outlet opening 23 of the separation fluid channel 21 rather than the inlet opening 22 thereof.

The emitted-light guiding unit 31 connects the light-emission control unit 35 that has a light source for emitting light and the optical fiber 33 together. The light source is, for example, an LED.

The received-light guiding unit 32 connects the light-reception control unit 36 that has a light receiving unit for receiving light and the optical fiber 34 together. The light receiving unit is, for example, a photo diode. The received-light guiding unit 32 may further include a light collecting function like a lens at the tip thereof.

The emitted-light guiding unit 31 and the received-light guiding unit 32 face with each other with the microchip 20 intervening therebetween, and are arranged so that respective optical fibers 33 and 34 are coaxial with each other. In order to improve the measurement precision, it is preferable that the misalignment between the optical axis of the emitted-light guiding unit 31 and that of the received-light guiding unit 32 should be small as much as possible.

As the light-emission control unit 35 controls the emitted-light guiding unit 31 and the light-reception control unit 36 controls the received-light guiding unit 32, respectively, the detecting unit 30 emits light from the emitted-light guiding unit 31 to the sample solution K, and the received-light guiding unit 32 receives transmissive light, thereby measuring a light absorption level. Next, an unillustrated arithmetic unit of the control unit 61 extracts a specific constituent based on the light absorption level or calculates the concentration of the specific constituent, and the analyzing process completes. The working of the analysis and measurement according to the present embodiment will be explained below.

Figure 5:
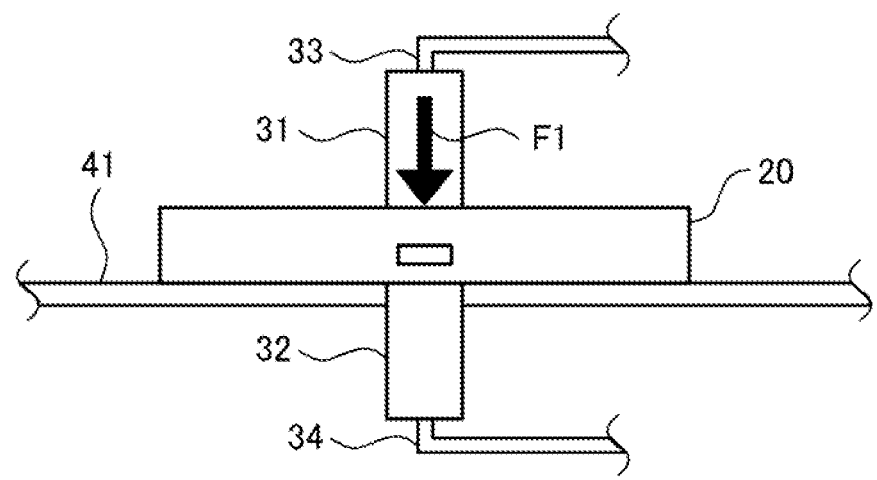
FIG. 5 is a schematic configuration diagram showing an illustrative analyzing-measuring unit of the analyzing apparatus according to the embodiment.

FIG. 5 is a schematic configuration diagram showing an illustrative analyzing-measuring unit of the analyzing apparatus according to the present embodiment. The microchip 20 is placed in advance on the microchip support table 41 of the analyzing-measuring unit 40. Moreover, the emitted-light guiding unit 31 and the received-light guiding unit 32 are laid out so as to hold therebetween the separation fluid channel 21 of the microchip 20. At this time, the emitted-light guiding unit 31 applies a predetermined restorative force (the force F1) to the microchip 20, so that a force (the force F1) that pushes the microchip 20 against the microchip support table 41 acts.

The emitted-light guiding unit 31 is placed at a position between the inlet opening 22 and the outlet opening 23 and slightly closer to the outlet opening 23 beyond the middle portion as viewed in a direction in which the fluid channel runs. The emitted-light guiding unit 31 applies a force (the force F1) that pushes down the microchip 20, in particular, the separation flow channel 21.

During analyzing, measuring and detecting processes by the analyzing apparatus 1, following effects act on the microchip 20. Since the analyzing and measuring processes are performed through electrophoresis, it is necessary to apply a voltage across the electrodes 24 and 25 at both ends of the separation fluid channel 21. A current generated by such a voltage causes a temperature rise of the microchip 20. In the detecting process, light emitted from the emitted-light guiding unit 31 is received by the received-light guiding unit 32, and the light is emitted to the separation fluid channel 21 in order to perform an arithmetic processing. At this time, heat is generated by light emission, causing a temperature rise of the microchip 20.

Because of the application of a voltage and the emission of light, the separation fluid channel 21 of the microchip 20 is subjected to a temperature rise, and the temperature rise becomes significant in the vicinity of, in particular, the location where light is measured. Since the microchip support table 41 is formed of a material with a high thermal conductivity like aluminum in order to facilitate heat dissipation, the surface of the microchip 20 contacting the microchip support table 41 has a temperature rise suppressed in comparison with the surface of the microchip 20 not facing the microchip support table 41. As a result, the surface of the microchip 20 not facing the microchip support table 41 is likely to be affected by the temperature rise, the microchip 20 produces a thermal expansion, and the microchip 20 is deformed convexly toward the emitted-light guiding member 31.

At this time, the emitted-light guiding unit 31 abuts the microchip 20, and applies a predetermined force (the force F1) to the microchip 20 by the restorative force of the coil spring 31c, and thus the microchip 20 is prevented from deforming convexly. By preventing the microchip 20 from deforming convexly, a deformation of the separation fluid channel 21 is also suppressed. By suppressing a deformation of the separation fluid channel, a change in the flow property and a change in the light transmissive direction are suppressed, and thus deterioration of the measurement precision is suppressed as a result. Moreover, the emitted-light guiding unit 31 and the microchip 20 can maintain a condition of contacting each other, the location where light is emitted becomes constant, and the optical distance in measurement becomes constant, so that deterioration of the measurement precision is suppressed.

Since the emitted-light guiding unit 31 applies a force to the microchip 20 in order to prevent the microchip 20 from deforming, the microchip 20 formed of a material which is likely to produce a deformation due to heat can be used. The microchip 20 of not only a glass but also a resin, such as a silicon resin, an acrylic resin like a methyl-methacrylate resin, a polystyrene resin, or a polycarbonate resin, can be used. Moreover, regarding a material with a low strength and which is likely to deform, since the emitted-light guiding unit 31 applies the force to the microchip 20 in order to prevent the microchip 20 from deforming, the microchip 20 formed of such a material can be used.

An operation of the analyzing apparatus 1 for an analysis will be explained below with reference to FIGS. 1 to 5.

Operations of respective units of the analyzing apparatus 1 are controlled by the control unit 61. The analyzing apparatus 1 performs an analyzing operation through successive controls by the control unit 61. The control unit 61 includes, for example, a CPU, a memory, an input/output interface, and the like.

The analyzing apparatus 1 is provided with the three-way valves 55 and 56. The three-way valves 55 and 56 each have three connecting ports, and the control unit 61 independently controls a communication status among those connecting ports and a block-off status among those.

The liquid reserve tank 11 and the sample tank 12 are connected to the fluid channel 51 or the fluid channel 53 through the three-way valves 55 and 56. The control unit 61 controls the opening/closing of the valves, and independently controls a communication status with the separation fluid channel 21 and a block-off status therewith. The fluid channel 51 is connected to the microchip 20, i.e., the separation fluid channel 21, and the fluid channel 53 is connected to the waste liquid tank 13.

The power supply 62 applies a voltage for performing an analysis through a capillary electrophoresis technique in the separation fluid channel 21, and is connected to the electrode 24 that is a positive terminal and the electrode 25 that is a negative terminal. The applied voltage is, for example, 1.5 kV or so, and a function of applying a reverse-polarity voltage with respect to the above-explained positive-negative relationship may be provided.

Regarding a separation by electrophoresis, first, the power supply 62 applies a voltage across the electrode 24 that is a positive terminal and the electrode 25 that is a negative terminal in response to an instruction from the control unit 61, and an electroosmotic flow of the migration solution from the electrode 24 to the electrode 25 is produced. At this time, a specific constituent has a movement produced in accordance with intrinsic electrophoresis mobility from the electrode 24 to the electrode 25.

In response to an instruction from the control unit 61, the analyzing-measuring unit 40 causes the light source to emit light through the emitted-light guiding unit 31 at a specific location of the separation fluid channel 21, and causes the received-light guiding unit 32 to receive transmissive light. More specifically, the light source like an LED of the light-emission control unit 35 emits light with a wavelength in the vicinity of 415 nm from the emitted-light guiding unit 31 through the optical fiber 33, and the photo diode, etc., of the light-reception control unit 36 receives the transmissive light from the received-light guiding unit 32 through the optical fiber 34. When a specific constituent passes through the specific location of the separation fluid channel 21, light (light absorption level) received by the light receiving unit changes, and the concentration of the specific constituent and the amount thereof can be detected based on such a change.

Heat is applied to the microchip 20 due to an application of the voltage to the separation fluid channel 21 for electrophoresis and an emission of light for measurement, and the microchip 20 is deformed due to a temperature rise. Since the microchip support table 41 is formed of a material with a high thermal conductivity like aluminum so as to facilitate heat dissipation, the temperature rise of the surface of the microchip 20 contacting the microchip support table 41 is suppressed in comparison with another surface of the microchip 20 not facing the microchip support table 41. As a result, the surface of the microchip 20 not facing the microchip support table 41 is likely to be affected by the temperature rise, the microchip 20 produces a thermal expansion, and is deformed convexly toward the emitted-light guiding unit 31.

When light is emitted through the emitted-light guiding unit 31 for measurement, the emitted-light guiding unit 31 abuts the microchip 20 and pushes down the microchip 20 with the force F1 while light is being emitted. More specifically, the coil spring 31$c$ is compressed by the stopper 31$d$ fixed to the shield wall 42. The ferrule 31$a$ that is the tip of the emitted-light guiding unit 31 is pressed against the microchip 20 by the force F1 that is the restorative force of the coil spring 31$c$, and the separation fluid channel 21 at the upper portion of the microchip 20 where measurement is performed is pushed toward the microchip support table 41.

The microchip 20 receives a force (the force F1) in a direction in which the convexly deformed portion is restored, so that the microchip 20 can be prevented from deforming. Since the separation fluid channel 21 does not deform, a change in the flow property in the separation fluid channel 21 and a change in the transmissive direction of emitted light, etc., due to a deformation are suppressed, resulting in suppression of the deterioration of the measurement precision. Moreover, the emitted-light guiding unit 31 and the microchip 20 can maintain the contacting condition, the location where light is emitted becomes constant, and the optical distance at the time of measurement becomes constant, thereby suppressing the deterioration of the measurement precision.

Moreover, the microchip 20 is placed inside the shield wall 42 so that the microchip 20 is not affected by heat from the light-emission control unit 35 and the light-reception control unit 36. As a result, the temperature rise of the microchip 20 can be reduced, thereby suppressing the deterioration of the measurement precision. Furthermore, by providing the shield wall 42, the stray-light eliminating effect by the analyzing-measuring unit 40 is enhanced, contributing to the improvement of the measurement precision.

Furthermore, the received-light guiding unit 32 and the light-reception control unit 36 are coupled together by the optical fiber 34, and the received-light guiding unit 32 and the light-reception control unit 36 are distant from each other, so that the received-light guiding unit 32 is not affected by heat from the light-reception control unit 36. As a result, even if the received-light guiding unit 32 is formed of a material that changes the photosensitivity due to a temperature of the photo diode, etc., it is possible to suppress the deterioration of the measurement precision.

An analysis result is stored in, for example, an unillustrated memory unit, and the analysis is terminated. Through the above-explained processes, an analysis using the analyzing apparatus 1 completes.

Figure 6:
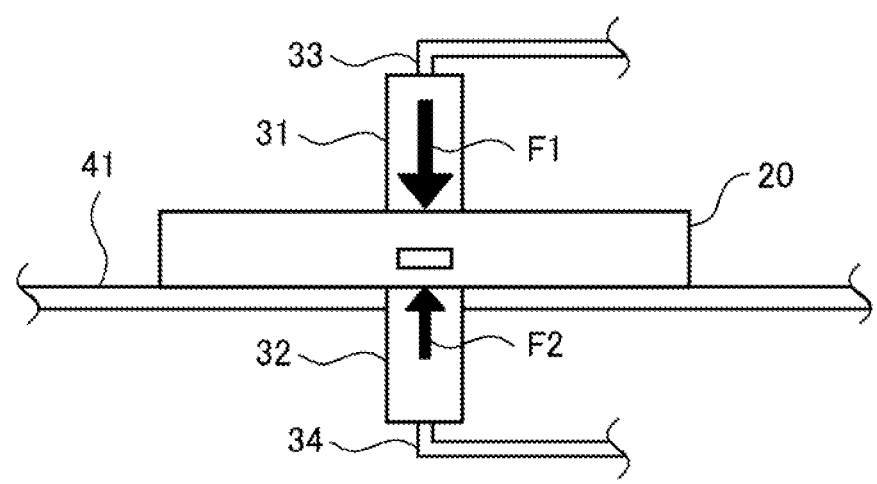
FIG. 6 is a schematic configuration diagram showing an illustrative analyzing-measuring unit of an analyzing apparatus according to a first modified embodiment.

FIG. 6 is a schematic configuration diagram showing an illustrative analyzing-measuring unit of an analyzing apparatus according to a first modified embodiment. The basic configuration is same as that of the analyzing apparatus 1 of the first embodiment, but the received-light guiding unit 32 uses a force-applying member like the emitted-light guiding unit 31 but has a smaller biasing force than that of the emitted-light guiding unit 31.

When a voltage is applied and light is emitted, the separation fluid channel 21 of the microchip 20 increases the temperature, and in particular, the portion in the vicinity of the light measured location is subjected to further significant temperature rise. Since the microchip support table 41 is formed of a material with a high thermal conductivity like aluminum in order to facilitate heat dissipation, the surface of the microchip 20 contacting the microchip support table 41 has the temperature rise suppressed in comparison with another surface of the microchip 20 not facing the microchip support table 41. As a result, another surface of the microchip 20 not facing the microchip support table 41 is likely to be affected by the temperature rise, the microchip 20 produces thermal expansion, and is deformed convexly toward the emitted-light guiding unit 31.

At this time, the emitted-light guiding unit 31 pushes the microchip 20 with a predetermined force (the force F1), and the microchip 20 is pressed against the microchip support table 41, thereby preventing the microchip 20 from producing a deformation convexly. The received-light guiding unit 32 simultaneously applies a predetermined force (the force F2) to the microchip 20 toward the emitted-light guiding unit 31, i.e., from the received-light guiding unit 32.

Since the received-light guiding unit 32 has a force-applying function like a spring, the microchip 20 can be held in a pressed manner. As a result, the emitted-light guiding unit 31 closely contacts and abuts the microchip 20, and the received-light guiding unit 32 opposite to the emitted-light guiding unit 31 closely contacts and abuts the microchip 20. Accordingly, the emitted-light guiding unit 31, the received-light guiding unit 32, and the microchip 20 are joined together, and the positional relationship (the optical distance) becomes constant, thereby suppressing deterioration of the measurement precision.

If a convex deformation produced by the microchip 20 cannot be suppressed by the force (the force F1) applied from the emitted-light guiding unit 31, and the microchip 20 produces a slight convex deformation, the received-light guiding unit 32 applies a predetermined force (the force F2) to the microchip 20. Accordingly, the emitted-light guiding unit 31, the received-light guiding unit 32, and the microchip 20 maintain their joined conditions as a whole. As a result, the positional relationship (the optical-distance) becomes constant, thereby suppressing deterioration of the measurement precision.

The same is true of the case of the first embodiment (see FIG. 5) when no force (the force F2) is applied from the received-light guiding unit 32.

Figure 7A:
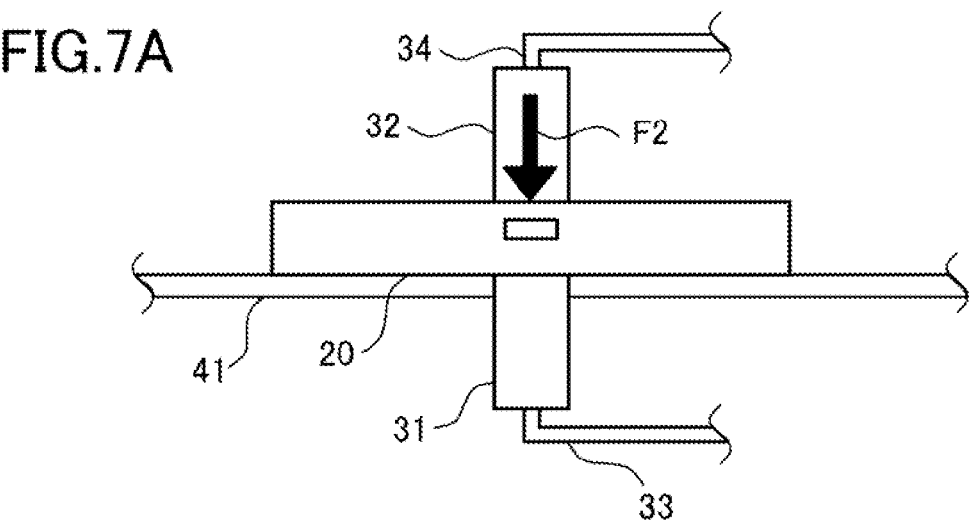
FIG. 7A is a schematic configuration diagram showing an illustrative analyzing-measuring unit of an analyzing apparatus according to a second modified embodiment.
Figure 7B:
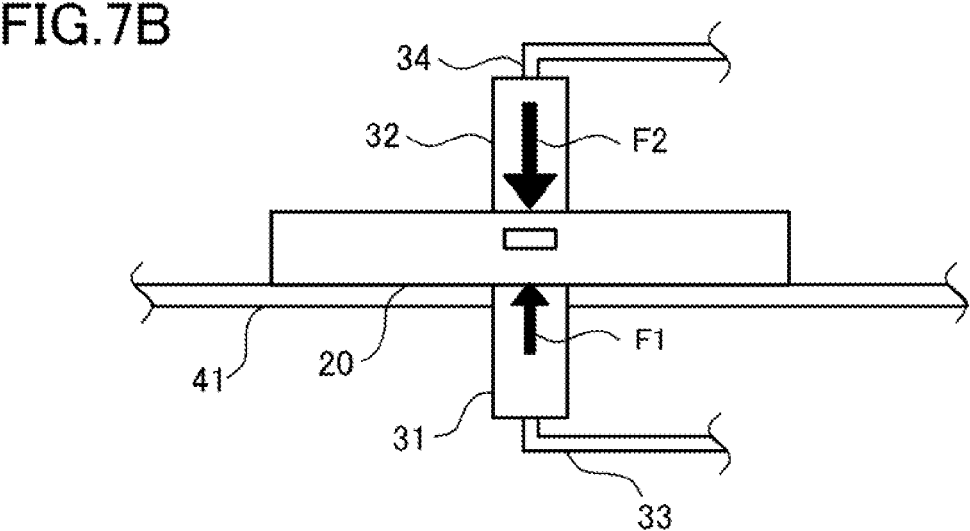
FIG. 7B is a schematic configuration diagram showing an illustrative analyzing-measuring unit of an analyzing apparatus according to the second modified embodiment.

FIGS. 7A and 7B are schematic configuration diagrams showing an illustrative analyzing-measuring unit of an analyzing apparatus according to a second modified embodiment. The basic configuration is same as that of the analyzing apparatus 1 of the first embodiment, but respective positions of the emitted-light guiding unit 31 and the received-light guiding unit 32 are inverted upside down. More specifically, the received-light guiding unit 32 is placed at a location facing the microchip support table 41 via the microchip 20, and the emitted-light guiding unit 31 is placed at the microchip-support-table-41 side. FIG. 7A corresponds to FIG. 5, and FIG. 7B corresponds to FIG. 6.

In the second modified embodiment, as shown in FIG. 7A, it is necessary to employ a force-applying member that pushes the microchip 20 toward the microchip support table 41. At least the received-light guiding unit 32 includes a force-applying member that pushes the microchip 20 with a predetermined force (the force F2).

Moreover, as shown in FIG. 7B, when not only the received-light guiding unit 32 but also the emitted-light guiding unit 31 include a force-applying member, such a force-applying member is designed so that a force (the force F1) applied by the emitted-light guiding unit 31 is weaker than a force (the force F2) applied by the received-light guiding unit 32. By increasing the force (the force F2) applied by the received-light guiding unit 32 in comparison with the force (the force F1) applied by the emitted-light guiding unit 31, the microchip 20 can be pushed toward the microchip support table 41.

Figure 8:
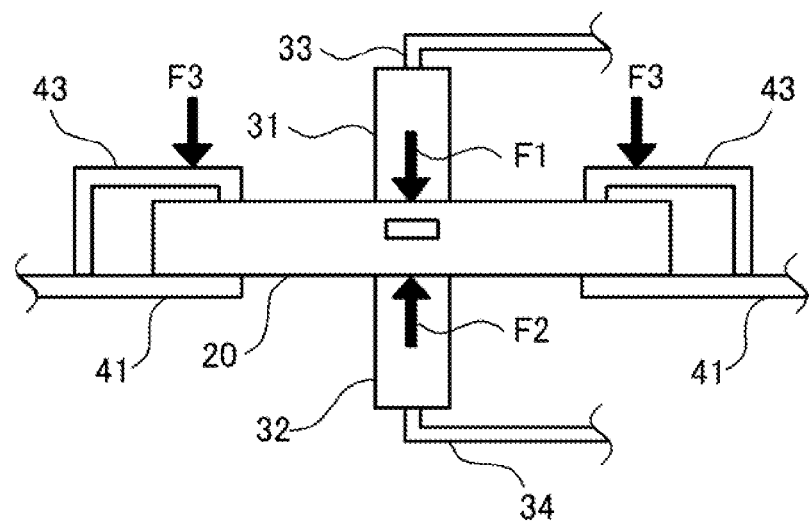
FIG. 8 is a schematic configuration diagram showing an illustrative analyzing-measuring unit of an analyzing apparatus according to a third modified embodiment.

FIG. 8 is a schematic configuration diagram showing an illustrative analyzing-measuring unit of an analyzing apparatus according to a third modified embodiment. The basic configuration is same as that of the analyzing apparatus 1 of the first embodiment, but microchip holders 43 are further added.

The microchip holders 43 are used when the fixing of the microchip 20 to the microchip support table 41 is insufficient, e.g., when the microchip 20 is formed of a light material like a resin and the fixing and holding of the microchip 20 are difficult. According to the present invention, the microchip holders 43 push the microchip 20 against the microchip support table 41 with predetermined forces (forces F3).

The emitted-light guiding unit 31 abuts the microchip 20, pushes the microchip 20 toward the microchip support table 41 with a predetermined force (the force F1), and the microchip holders 43 also push the microchip 20 toward the microchip support table 41 with predetermined forces (the forces F3). As a result, when the microchip 20 produces a convex deformation at the time of analysis, the microchip 20 is pushed by the emitted-light guiding unit 31 and the microchip holders 43, thereby preventing the microchip 20 from producing a deformation. At this time, it is fine if the predetermined force (the force F1) applied by the emitted-light guiding unit 31 is smaller than the force applied only by the emitted-light guiding unit 31.

Regarding the case in which the microchip 20 is pushed by the received-light guiding unit 32 with the predetermined force (the force F2), when no microchip holder 43 is used, it is necessary that the predetermined force (the force F1) applied by the emitted-light guiding unit 31 should be larger than the predetermined force (the force F2) applied by the received-light guiding unit 32, but those forces may be substantially equal. By using the microchip holders 43, the microchip 20 is pushed toward the microchip support table 41 in order to prevent the microchip 20 from producing a convex deformation. As a result, a deformation of the microchip 20 can be suppressed, thereby suppressing deterioration of the measurement precision. Furthermore, the microchip 20 (including the separation fluid channel 21 where light is measured) is held between the emitted-light guiding unit 31 and the received-light guiding unit 32, and the optical distance is maintained at constant, thereby improving the precision of measurement.

Figure 9A:
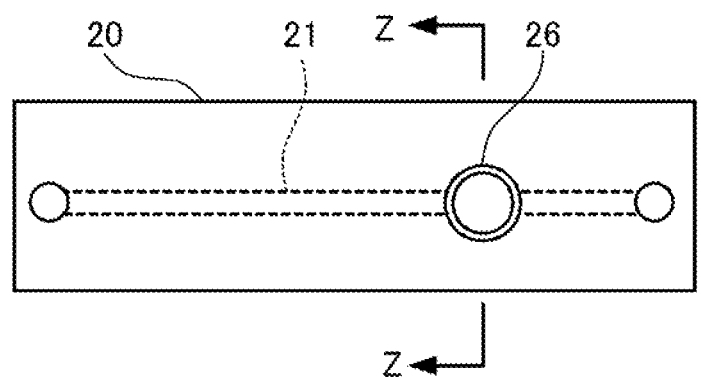
FIG. 9A is a schematic configuration diagram showing an illustrative microchip of the embodiment.

FIG. 9A is a schematic configuration diagram showing an illustrative microchip of an analyzing apparatus according to another embodiment. The microchip 20 has a guide (a recess) 26 formed in the upper part of the separation fluid channel 21 where the detecting unit 30 is provided. The emitted-light guiding unit 31 can be fitted in the guide 26 with a clearance.

Figure 9B:
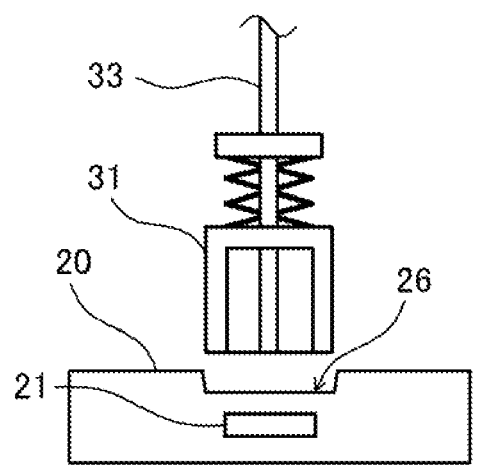
FIG. 9B is a cross-sectional view taken along a line Z-Z in FIG. 9A.

FIG. 9B is a cross-sectional view taken along a line Z-Z in FIG. 9A. The guide 26 is formed in the predetermined part above the separation fluid channel 21, and the emitted-light guiding unit 31 can emit light to a predetermined portion of the separation fluid channel 21. As a result, by only fitting the emitted-light guiding unit 31 into the guide 26, light can be emitted to a predetermined location without a positioning, and thus the microchip 20 can be easily placed on the microchip support table 41. Moreover, since the location where light is emitted is fixed, the optical distance at the time of measurement becomes constant, so that measurement becomes stable.

Furthermore, by using the microchip 20 with the guide 26, when the emitted-light guiding unit 31 applies a force to the microchip 20, the pushed and pressed position is fixed, so that a force can be stably applied. By applying a certain constant force to the microchip 20 through a predetermined detection location, stable measurement, i.e., stable light emission and light receiving are enabled.

As explained above, according to the analyzing apparatus of the above-explained embodiments, it is possible to reduce a thermal effect and to suppress deterioration of the measurement precision.

In a detection of a specific constituent, when light is emitted to the separation fluid channel of the microchip, a force is applied to the microchip directly from the light emitting unit, and thus a deformation of the microchip and that of the separation fluid channel due to heat are suppressed. Accordingly, a change in the flow property and a change in the transmissive light of emitted light, etc., in the separation fluid channel are suppressed, thereby suppressing deterioration of the measurement precision. Moreover, by applying a force to the microchip directly from the light emitting unit, a distance between the light guiding units with the microchip intervening therebetween can be maintained at constant, the optical distance becomes constant, thereby suppressing deterioration of the measurement precision.

Moreover, the light guiding unit and the light-reception control unit which abut or are located near the microchip (the separation fluid channel) are laid out so as to be distant from each other through the optical fiber. Accordingly, the light receiving unit like a photo diode can be distant from the light-reception control unit. As a result, a change in the photosensitivity of the photo diode due to heat can be reduced, thereby suppressing deterioration of the measurement precision.

Furthermore, the light guiding unit and the light emission or light-reception control unit which abut or are located near the microchip (the separation fluid channel) are placed so as to be distant from each other, a thermal effect to the microchip is reduced, resulting in suppression of the deterioration of the measurement precision originating from moistened spots of the buffer solution. A change in the sample caused at a temperature equal to or higher than the predetermined temperature, e.g., a coagulation of protein under a high temperature condition is reduced, thereby suppressing deterioration of the measurement precision.

The analyzing apparatus of the above-explained embodiments is not limited to the examples explained above. The specific configuration of the analyzing apparatus of the present invention can be designed, changed and modified in various forms. For example, the structure of the fluid channel, the number of reserve tanks, respective layouts of the functions and shapes thereof can be designed in accordance with the application of the analyzing apparatus. Regarding an analysis using the analyzing apparatus, at least any one of the following optical analysis indexes can be applied to the analysis: a reflection ratio; a transmittance; a light absorbancy; fluorescence; and luminescence.

The deformation of the microchip explained in the above embodiments is merely an example. The shape of deformation of the microchip, the deformation level and the direction of deformation vary depending on various factors, such as the kind of an analyzing apparatus, an analysis method, an analysis target, and a microchip to be used. According to the above-explained embodiments, it is appropriate as far as a force is applied through the light emitting unit and/or the light receiving unit so that the microchip is pushed toward the support member in order to prevent the microchip from producing a deformation, and the present invention is not limited to the above-explained examples. Moreover, the magnitude of an applied force can be set arbitrary in accordance with the material of the microchip, the analysis temperature, a difference between a force applied by the light emitting unit and a force applied by the light receiving unit, and the direction of the applied force.

The force-applying member of applying a force through a light guiding unit in an analysis is not limited to the coil spring but may be other elastic bodies like a plate spring. Moreover, the location where the light guiding unit is placed relative to the microchip (the separation fluid channel) is not limited to the above-explained examples. It is preferable that the coaxial level between the optical axis of light emission and that of light reception should be small as much as possible when the light guiding units are placed.

The material of the microchip is not limited to a resin, but may be, for example, a glass. The number of separation fluid channels of the microchip is not limited to one, and may be plural. The structure of the separation fluid channel is not limited to a straight shape, but may be a so-called cross-injection shape with two fluid channels intersecting with each other.

Furthermore, preferred embodiments of the present invention include following configurations.

Regarding the analyzing apparatus of the present invention, it is preferable that the light emitting unit should include a light-emission control unit with a light source and a first light guiding unit that guides light from the light-emission control unit to the light measuring part.

It is preferable that the light receiving unit should include a light-reception control unit and a second light guiding unit that guides light which has gone through the light measuring part to the light-reception control unit.

It is preferable that the light emitting unit should include a light-emission control unit with a light source and a first light guiding unit that guides light from the light-emission control unit to the light measuring part, the light receiving unit should include a light-reception control unit and a second light guiding unit that guides light which has gone through the light measuring part to the light-reception control unit, and the analyzing apparatus should further comprise a control unit configured as a single unit by the light-emission control unit and the light-reception control unit.

It is preferable that the first light guiding unit and/or the second light guiding unit should include an optical fiber.

It is preferable that the first light guiding unit and/or the second light guiding unit should include at least any one of followings: a lens; a filter; and a housing.

It is preferable that the light emitting unit or the light receiving unit including no first force-applying member should be placed so as to abut the microchip.

It is preferable that the light emitting unit or the light receiving unit including no first force-applying member should comprise a second force-applying member that applies a force to the microchip.

It is further preferable that the light emitting unit or the light receiving unit including a second force-applying member should be placed at the support-member side of the microchip, and the second force-applying member should apply a force which is smaller than a force applied by the first force-applying member to the microchip in a direction opposite to a direction of the force applied by the first force-applying member.

It is preferable that the first force-applying member and/or the second force-applying member should include an elastic member.

It is further preferable that the elastic member should include a spring mechanism.

It is preferable that the light receiving unit should include a photo diode.

It is preferable that the microchip should be formed of a light-transmissive material formed with a fluid channel, and the light measuring part should be the fluid channel.

It is further preferable that the microchip should be formed of a resin.

It is preferable that an analysis should be performed using at least one of following optical analysis indexes: a reflection ratio; a transmittance; a light absorbancy; fluorescence; and luminescence.

Having described and illustrated the principles of this application by reference to one or more preferred embodiments, it should be apparent that the preferred embodiments may be modified in arrangement and detail without departing from the principles disclosed herein and that it is intended that the application be construed as including all such modifications and variations insofar as they come within the spirit and scope of the subject matter disclosed herein.

What is claimed is:

1. An analyzing apparatus comprising:
a microchip including a light measuring part;
a support member that supports the microchip;
a light emitting unit that emits light to the light measuring part;
a light receiving unit that receives light which has gone through the light measuring part; and
a first force-applying member which causes the light emitting unit or the light receiving unit that is placed at a position facing the support member via the microchip to abut the microchip and to push the microchip in a direction in which the microchip is supported by the support member, wherein the first force-applying member includes an elastic member.

2. The analyzing apparatus according to claim 1, wherein the light emitting unit includes a light-emission control unit with a light source and a first light guiding unit that guides light from the light-emission control unit to the light measuring part.

3. The analyzing apparatus according to claim 2, wherein the light receiving unit includes a light-reception control unit and a second light guiding, unit that guides light which has gone through the light measuring part to the light-reception control unit.

4. The analyzing apparatus according to claim 2, wherein the first light guiding unit includes an optical fiber.

5. The analyzing apparatus according to claim 2, wherein the first light guiding unit includes at least any one of followings: a lens; a filter; and a housing.

6. The analyzing apparatus according to claim 1, wherein the light receiving unit includes a light-reception control unit and a second light guiding unit that guides light which has gone through the light measuring part to the light-reception control unit.

7. The analyzing apparatus according to claim 6, wherein the second light guiding unit includes an optical fiber.

8. The analyzing apparatus according to claim 6, wherein the second light guiding unit includes at least any one of followings: a lens; a filter; and a housing.

9. The analyzing apparatus according to claim 1, wherein
the light emitting unit includes a light-emission control unit with a light source and a first light guiding unit that guides light from the light-emission control unit to the light measuring part,
the light receiving unit includes a light-reception control unit and a second light guiding unit that guides light which has gone through the light measuring part to the light-reception control unit, and
the analyzing apparatus further comprises a control unit configured as a single unit by the light-emission control unit and the light-reception control unit.

10. The analyzing apparatus according to claim 1, wherein the light emitting unit or the light receiving unit including no first force-applying member is placed so as to abut the microchip.

11. The analyzing apparatus according to claim 1, wherein the light emitting unit or the light receiving unit including no first force-applying member comprises a second force-applying member that applies a three to the microchip.

12. The analyzing apparatus according to claim 11, wherein
the light emitting unit or the light receiving unit including no second force-applying member is placed at the support-member side of the microchip, and
the second force-applying member applies a force which is smaller than a force applied by the first force-applying member to the microchip in a direction opposite to a direction of the force applied by the first force-applying member.

13. The analyzing apparatus according to claim 1, wherein the elastic member includes a spring mechanism.

14. The analyzing apparatus according to claim 1, wherein the light receiving unit includes a photo diode.

15. The analyzing apparatus according to claim 1, wherein
the microchip is formed of a light-transmissive material formed with a fluid channel, and
the light measuring part is the fluid channel.

16. The analyzing apparatus according to claim 15, wherein the microchip is formed of a resin.

17. The analyzing apparatus according to claim 1, performing an analysis using at least one of following optical analysis indexes: a reflection ratio; a transmittance; a light absorbancy; fluorescence; and luminescence.

18. An analyzing apparatus, comprising:
a microchip including a light measuring part;
a support member that supports the microchip;
a light emitting unit that emits light to the light measuring part;
a light receiving unit that receives light which has gone through the light measuring part; and
a first force-applying member which causes the light emitting unit or the light receiving unit that is placed at a position facing the support member via the microchip to abut the microchip and to push the microchip in a direction in which the microchip is supported by the support member,
wherein the light emitting unit or the light receiving unit including no first force-applying member comprises a second force-applying member that applies a force to the microchip; and
the second force-applying member includes an elastic member.

19. An analyzing apparatus, comprising:
a microchip including a light measuring part;
a support member that supports the microchip;
a light emitting unit that emits light to the light measuring part;
a light receiving unit that receives light which has gone through the light measuring part; and
a first force-applying member which causes the light emitting unit or the light receiving unit that is placed at a position facing the support member via the microchip to abut the microchip and to push the microchip in a direction in which the microchip is supported by the support member,
wherein the light emitting unit or the light receiving unit including no first force-applying member comprises a second force-applying member that applies a force to the microchip; and
the first force-applying member and the second force-applying member each include an elastic member.

* * * * *